US010960162B2

(12) United States Patent
Sinderby et al.

(10) Patent No.: US 10,960,162 B2
(45) Date of Patent: Mar. 30, 2021

(54) DEVICE AND METHOD FOR CONTROLLING VENTILATORY ASSIST

(71) Applicant: St. Michael's Hospital, Toronto (CA)

(72) Inventors: Christer Sinderby, Toronto (CA); Jennifer Beck, Toronto (CA); Norman Comtois, Scarborough (CA)

(73) Assignee: UNITY HEALTH TORONTO

( * ) Notice: Subject to any disclaimer, the term of this patent is extended or adjusted under 35 U.S.C. 154(b) by 221 days.

(21) Appl. No.: 16/067,220

(22) PCT Filed: Dec. 29, 2016

(86) PCT No.: PCT/CA2016/051549
§ 371 (c)(1),
(2) Date: Jun. 29, 2018

(87) PCT Pub. No.: WO2017/113017
PCT Pub. Date: Jul. 6, 2017

(65) Prior Publication Data
US 2019/0015615 A1    Jan. 17, 2019

Related U.S. Application Data

(60) Provisional application No. 62/273,527, filed on Dec. 31, 2015.

(51) Int. Cl.
*A61M 16/00*    (2006.01)
*A61B 5/091*    (2006.01)
(Continued)

(52) U.S. Cl.
CPC ......... *A61M 16/026* (2017.08); *A61B 5/0488* (2013.01); *A61B 5/08* (2013.01);
(Continued)

(58) Field of Classification Search
CPC .............. A61M 16/0003; A61M 16/02; A61M 16/021; A61M 16/024; A61M 16/026;
(Continued)

(56) References Cited

U.S. PATENT DOCUMENTS 6,390,092 B1 *   5/2002   Leenhoven ....... A61M 16/0096
                                                128/204.23
6,679,258 B1 *   1/2004   Strom ................. A61M 16/026
                                                128/204.21
(Continued)

FOREIGN PATENT DOCUMENTS

WO    2007/082384 A1    7/2007
WO    2010/081223 A1    7/2010
WO    2010/081230 A1    7/2010

OTHER PUBLICATIONS

Supplementary European Search Report for EP Application No. EP 16 88 0225, date of completion Jul. 12, 2019, 2 pages.
(Continued)

*Primary Examiner* — Valerie L Woodward
*Assistant Examiner* — Paige Kathleen Bugg
(74) *Attorney, Agent, or Firm* — K&L Gates LLP

(57) ABSTRACT

A device and method for controlling a level of ventilatory assist applied to a patient by a mechanical ventilator measures, during patient's assisted breath, an inspiratory volume $V_{assist}$ produced by both the patient and the mechanical ventilator, an inspiratory volume $V_{vent}$ contributed by the mechanical ventilator, and an inspiratory assist pressure $P_{vent}$ produced by the mechanical ventilator. A first relation between pressure $P_{vent}$ and volume $V_{assist}$ and a second relation between pressure $P_{vent}$ and volume $V_{vent}$ are calculated. Using the first and second relations, a ratio is determined between pressure $P_{vent}$ at volume $V_{vent}$ and pressure $P_{vent}$ at volume $V_{assist}$, with volume $V_{vent}$ equal to volume $V_{assist}$, for a plurality of volumes $V_{vent}$ and $V_{assist}$. Values of
(Continued)

$P_{vent}$ are multiplied by the corresponding calculated ratios to calculate a third relation between a predicted inspiratory pressure $P_{pred}$ and volume $V_{assist}$. The mechanical ventilator is responsive to the third relation to control the level of ventilatory assist.

26 Claims, 11 Drawing Sheets

(51) Int. Cl.
A61B 5/08 (2006.01)
A61B 5/0488 (2006.01)
A61B 5/00 (2006.01)
(52) U.S. Cl.
CPC ............ *A61B 5/091* (2013.01); *A61M 16/024* (2017.08); *A61B 5/40* (2013.01); *A61B 5/6852* (2013.01); *A61B 5/7275* (2013.01); *A61M 2016/003* (2013.01); *A61M 2016/0027* (2013.01); *A61M 2016/0039* (2013.01); *A61M 2205/52* (2013.01); *A61M 2230/40* (2013.01); *A61M 2230/60* (2013.01)
(58) Field of Classification Search
CPC .... A61M 2016/0027; A61M 2016/003; A61M 2016/0036; A61M 2016/0039; A61M 2016/0042; A61M 2205/52; A61M 2230/40; A61M 2230/42; A61M 2230/46; A61M 2230/52; A61M 2230/63; A61B 5/00; A61B 5/00036; A61B 5/0004; A61B 5/0048; A61B 5/04012; A61B 5/0488; A61B 5/08; A61B 5/40; A61B 5/6852; A61B 5/7575; A61B 5/7278; G06F 19/00; G06F 19/30

See application file for complete search history.

(56) References Cited

U.S. PATENT DOCUMENTS

| | | | |
|---|---|---|---|
| 2007/0151563 A1 | 7/2007 | Ozaki et al. | |
| 2009/0114224 A1* | 5/2009 | Handzsuj | A61M 16/0069 128/204.23 |
| 2010/0228142 A1* | 9/2010 | Sinderby | A61M 16/026 600/533 |
| 2010/0307499 A1* | 12/2010 | Eger | A61B 5/085 128/204.23 |
| 2011/0301482 A1* | 12/2011 | Sinderby | A61B 5/087 600/529 |
| 2012/0006327 A1* | 1/2012 | Sinderby | A61M 16/026 128/204.23 |
| 2012/0103334 A1* | 5/2012 | Sinderby | A61M 16/0051 128/204.18 |
| 2014/0373845 A1* | 12/2014 | Dong | A61B 5/087 128/204.23 |
| 2015/0090264 A1* | 4/2015 | Dong | A61B 5/4836 128/204.23 |
| 2017/0165480 A1* | 6/2017 | O'Mahony | A61N 1/36146 |
| 2019/0269911 A1* | 9/2019 | O'Mahony | A61N 1/3601 |

OTHER PUBLICATIONS

PCT International Search Report and The Written Opinion of the International Searching Authority for International Application No. PCT/CA2016/051549, dated Feb. 14, 2017, 8 pages.

* cited by examiner

DEVICE AND METHOD FOR CONTROLLING VENTILATORY ASSIST

CROSS REFERENCE TO RELATED APPLICATIONS

This application is a national phase under 35 U.S.C. § 371 of International Application No. PCT/CA2016/051549 filed on Dec. 29, 2016, which claims priority to and benefit of U.S. Provisional Application No. 62/273,527 filed on Dec. 31, 2015, the entire disclosures of each of which are incorporated by reference herein.

TECHNICAL FIELD

The present disclosure relates to a device and method for controlling a level of ventilatory assist applied to a patient by a mechanical ventilator.

BACKGROUND

In patients with acute respiratory failure who actively participate in inspiration while receiving mechanical ventilatory assist, the mechanical ventilatory assist is synchronized with inspiratory efforts. Also, the patient's respiratory function and the load of breathing are assessed in order to adequately adjust the mechanical ventilatory assist. Traditionally, determination of the mechanics of the patient's respiratory system has been performed during patient's respiratory muscle inactivity, for example induced by deep sedation and hyperventilation or paralysis, allowing the mechanical ventilator to apply pressure to the patient's respiratory system in order to inflate the patient's lungs without contribution from the respiratory muscles. The obtained data can be presented as pressure/volume curves showing the pressures required to inflate the patient's respiratory system. The pressure/volume curves can be used to describe mechanics of the patient's respiratory system such as compliance (for example ml/cmH$_2$O) or elastance (for example cmH$_2$O/ml) as well as resistance (cmH$_2$O/ml/s). Also, the shape of the pressure/volume curves provides information about inflection points during the inspiration phase related to steps in patient's lung recruitment.

Measurement of respiratory system mechanics in mechanically ventilated patients that actively participate in inspiration introduces an error since the inspiratory volume generated by the patient appears in the volume measurement while the pressure of the patient is not available unless pressure sensors, for example esophageal catheter pressure sensors, are introduced into the patient's respiratory system to measure lung distending pressure; however this measurement does not include the patient's effort/force used to expand the chest wall, i.e. the patient's rib-cage and abdomen. Hence, in the absence of patient's pressure measurement, the larger the patient's own inspiratory volume generation the larger the error of the measured pressure/volume curve.

The patient's neural activation of respiratory muscles reflects the force applied by these muscles. Hence, if two non-assisted breaths (no mechanical ventilation) have the same neural activation they should provide the same inspiratory volume (no inspiratory pressure would be available). If mechanical ventilation is applied to one of the two breaths with the same neural activation, the assisted breath will provide inspiratory pressure (generated by the mechanical ventilator) and its inspiratory volume will be increased compared to the non-assisted breath. Given that both breaths have the same neural activation one can assume that the force to expand the patient's respiratory system and inflate the lungs was similar during both breaths. It should however be reminded that some effects on force generation occur during assisted breath due to change in lung volume affecting muscle length/tension and added flow assist affecting force/velocity relationship.

Taking advantage of neural activation, using for example diaphragm electrical activity (EAdi), the diaphragm being the main respiratory muscle, there is a need to adjust/standardize the pressure/volume curve by removing the patient's effort and inspiratory volume generation (observed during the non-assisted breath) from that of the assisted breath (patient+ventilator inspiratory volume but only ventilator-generated inspiratory pressure), allowing 1) a trustworthy pressure/volume curve or relationship to describe the patient's respiratory system and 2) determine the mechanical pressure and EAdi required to inflate the patient's respiratory system to a given inspiratory volume. The present disclosure aims at providing a controller of a mechanical ventilator with such data.

SUMMARY

As a solution and according to a first aspect, the present disclosure provides a method for controlling a level of ventilatory assist applied to a patient by a mechanical ventilator, comprising (a) measuring, during patient's assisted breath, an inspiratory volume $V_{assist}$ produced by both the patient and the mechanical ventilator, an inspiratory volume $V_{vent}$ contributed by the mechanical ventilator, and an inspiratory assist pressure $P_{vent}$ produced by the mechanical ventilator; (b) calculating a first relation between pressure $P_{vent}$ and volume $V_{assist}$; (c) calculating a second relation between pressure $P_{vent}$ and volume $V_{vent}$; (d) using the first and second relations, calculating a ratio between pressure $P_{vent}$ at volume $V_{vent}$ and pressure $P_{vent}$ at volume $V_{assist}$, with volume $V_{vent}$ equal to volume $V_{assist}$, for a plurality of volumes $V_{vent}$ and $V_{assist}$; (e) multiplying values of $P_{vent}$ by the corresponding calculated ratios to calculate a third relation between a predicted inspiratory pressure the $P_{pred}$ and volume $V_{assist}$; and (f) controlling the mechanical ventilator using the third relation to control the level of ventilatory assist.

According to a second aspect, there is provided a device for controlling a level of ventilatory assist applied to a patient by a mechanical ventilator, comprising (a) at least one first detector, during patient's assisted breath, of an inspiratory volume $V_{assist}$ produced by both the patient and the mechanical ventilator, and an inspiratory volume $V_{vent}$ contributed by the mechanical ventilator; (b) a sensor of an inspiratory assist pressure $P_{vent}$ produced by the mechanical ventilator; (c) a first calculator of a first relation between pressure $P_{vent}$ and volume $V_{assist}$; (d) a second calculator of a second relation between pressure $P_{vent}$ and volume $V_{vent}$; (e) a third calculator, using the first and second relations, of a ratio between pressure $P_{vent}$ at volume $V_{vent}$ and pressure $P_{vent}$ at volume $V_{assist}$, with volume $V_{vent}$ equal to volume $V_{assist}$, for a plurality of volumes $V_{vent}$ and $V_{assist}$; (f) a multiplier of values of $P_{vent}$ by the corresponding calculated ratios to calculate a third relation between a predicted inspiratory pressure $P_{pred}$ and volume $V_{assist}$; and (g) a controller of the mechanical ventilator using the third relation to control the level of ventilatory assist.

According to a third aspect, there is provided a device for controlling a level of ventilatory assist applied to a patient by a mechanical ventilator, comprising (a) at least one first detector, during patient's assisted breath, of an inspiratory volume $V_{assist}$ produced by both the patient and the mechanical ventilator, and an inspiratory volume $V_{vent}$ contributed by the mechanical ventilator; (b) a sensor of an inspiratory assist pressure $P_{vent}$ produced by the mechanical ventilator; (c) at least one processor; and a memory coupled to the processor and comprising non-transitory instructions that when executed cause the processor to implement: a first calculator of a first relation between pressure $P_{vent}$ and volume $V_{assist}$; a second calculator of a second relation between pressure $P_{vent}$ and volume $V_{vent}$; a third calculator, using the first and second relations, of a ratio between pressure $P_{vent}$ at volume $V_{vent}$ and pressure $P_{vent}$ at volume $V_{assist}$, with volume $V_{vent}$ equal to volume $V_{assist}$, for a plurality of volumes $V_{vent}$ and $V_{assist}$; and a multiplier of values of $P_{vent}$ by the corresponding calculated ratios to calculate a third relation between a predicted inspiratory pressure $P_{pred}$ and volume $V_{assist}$; and (d) a controller of the mechanical ventilator using the third relation to control the level of ventilatory assist.

The foregoing and other objects, advantages and features of the present disclosure will become more apparent upon reading of the following non-restrictive description of illustrative embodiments thereof, given by way of example only with reference to the accompanying drawings.

DETAILED DESCRIPTION

The ventilatory assist level controlling device 900 and method 1000 will be described concurrently with reference to FIGS. 9 and 10.

Figure 9:
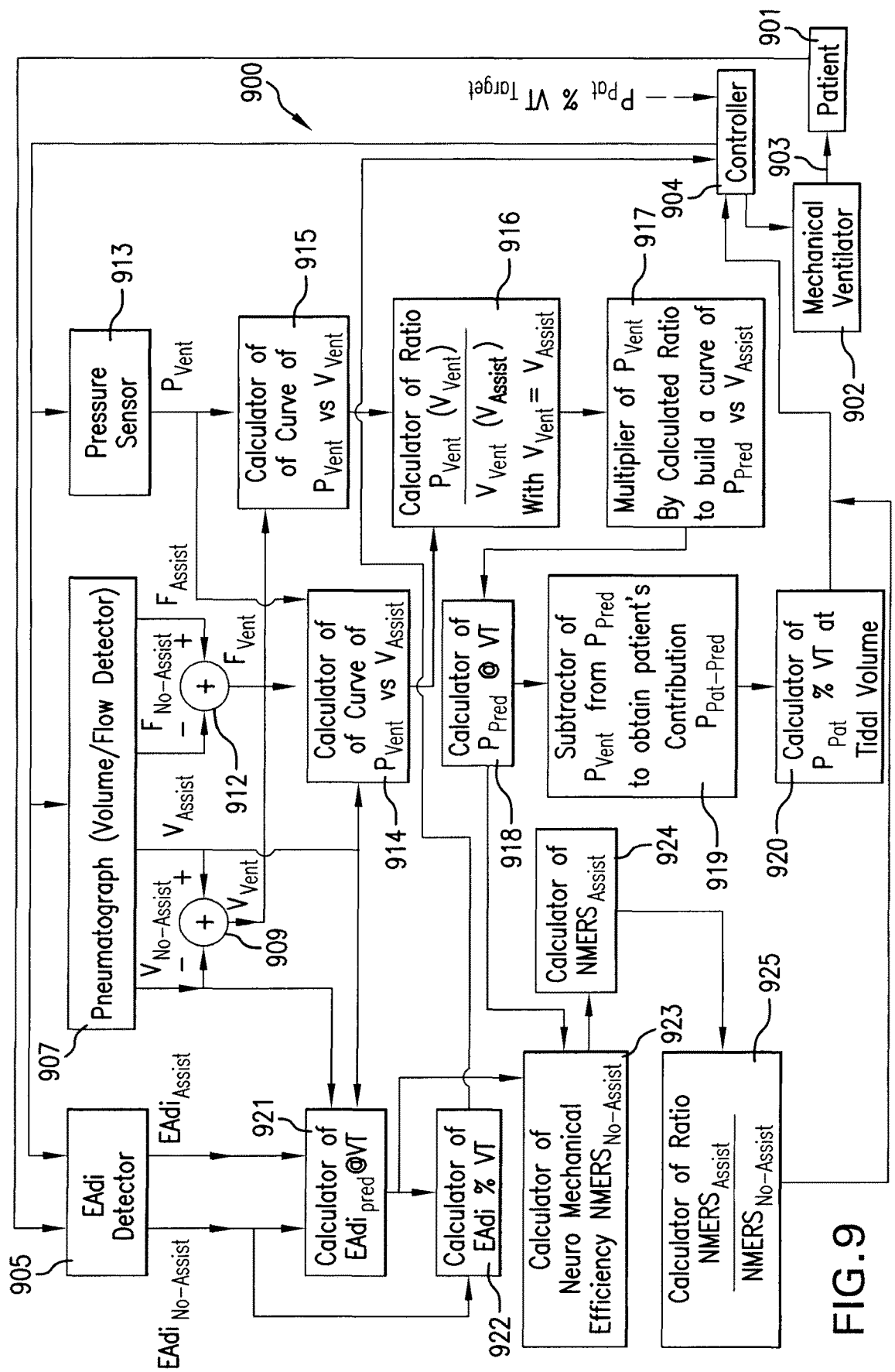
FIG. 9 is a block diagram of the ventilatory assist level controlling device according to one embodiment.
Figure 10:
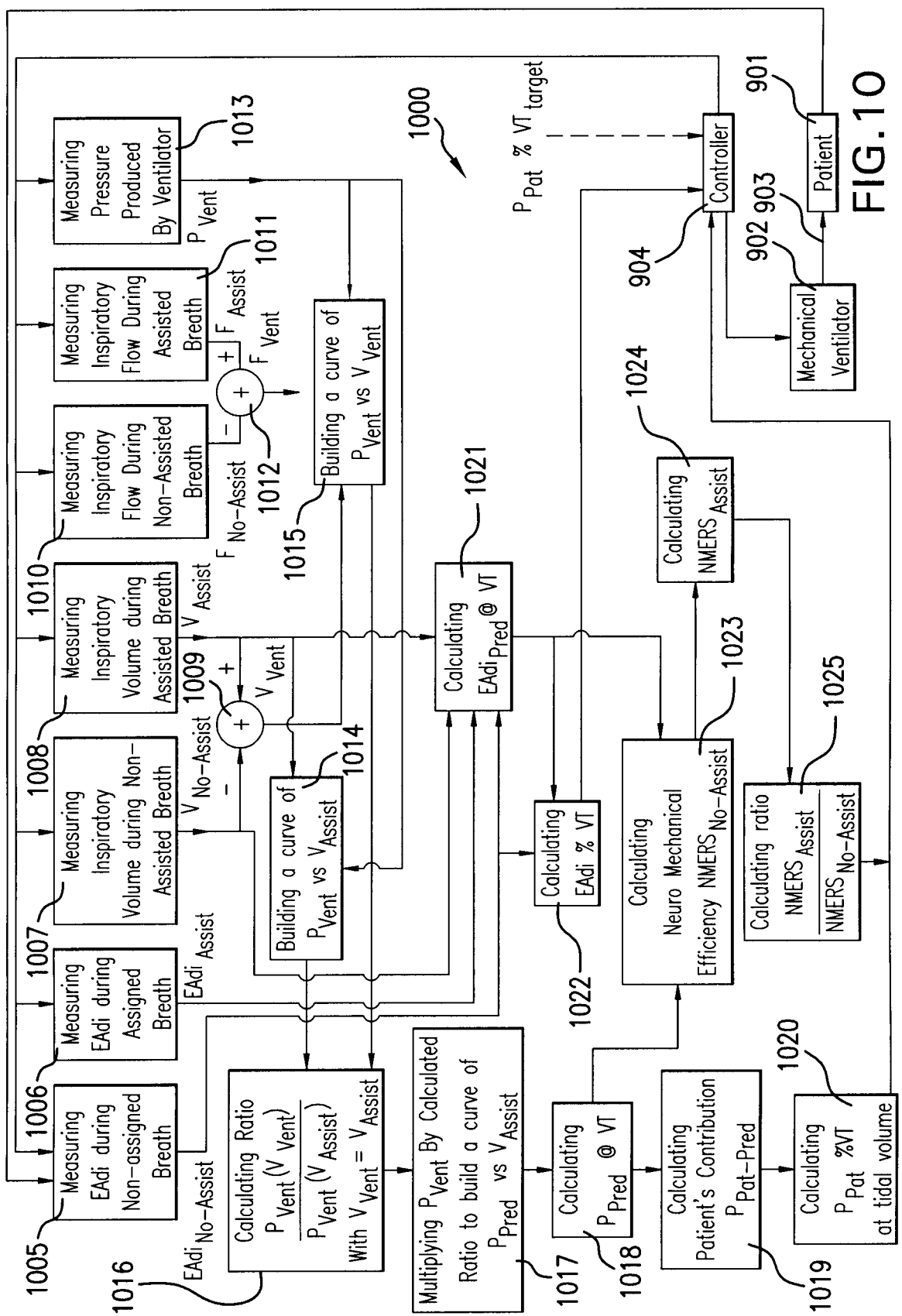
FIG. 10 is a flow chart of the ventilatory assist level controlling method according to one embodiment.

Referring to FIGS. 9 and 10, a patient 901 is connected to a mechanical ventilator 902 to receive ventilatory assist. For example, the patient 901 may be intubated and connected to the mechanical ventilator 902 through appropriate tubing 903. Alternatively, intubation may be replaced by a respiratory mask (not shown) through which ventilatory assist from the mechanical ventilator 902 is supplied to the patient 901. Specifically, as described in U.S. Pat. No. 5,820,560, of which the full contents is incorporated herein by reference, the mechanical ventilator 902 comprises a system (not shown) for supplying a breathable gas to the patient 901 through the tubing 903 and the intubation or respiratory mask.

The mechanical ventilator 902 is controlled by a controller 904. The controller 904 may be integrated to the mechanical ventilator 902 or provided as a separate unit. Also, the ventilatory assist level controlling device 900 may be integrated to the controller 904 or provided as a separate unit.

In the ventilatory assist level controlling device 900 and method 1000, the controller 904 may be based on the so-called NAVA (Neurally Adjusted Ventilatory Assist) mechanical ventilatory assist mode as described in U.S. Pat. No. 5,820,560. NAVA not only synchronizes the operation of the mechanical ventilator 902 with patient's inspiratory effort, but also controls the mechanical ventilator 902 to deliver positive assist pressure in proportion to electrical activity of a patient's respiratory muscle, for example the patient's diaphragm electrical activity (EAdi). Specifically, the magnitude of the pressure assist supplied by the mechanical ventilator 902 to the patient 901 is adjusted by a gain factor which converts the electrical activity of the patient's respiratory muscle, for example EAdi, into an assist pressure level; this gain factor is the so-called NAVA level. Of course, it is within the scope of the present disclosure to use electrical activity of a respiratory muscle other than the patient's diaphragm. Also within the scope of the present disclosure is the use of a physiological signal similar to electrical activity EAdi.

To perform measurements of parameters during a non-assisted breath, the controller 904 commands the mechanical ventilator 902 to provide no ventilatory assist during that breath (non-assisted breath). The controller 904 then signals to the corresponding sensors/detectors that the current breath is a non-assisted breath. Data from a number of non-assisted breaths can be stored for a better representation of such data.

In the same manner, the controller 904 signals to the sensors/detectors when a current breath is an assisted breath, i.e. a breath during which the mechanical ventilator 902 provides ventilatory assist to the patient.

During an operation 1005 of measuring EAdi during the non-assisted breath (EAdi$_{no\text{-}assist}$), an EAdi detector 905 measures EAdi$_{no\text{-}assist}$. In the same manner, the EAdi detector 905 measures EAdi during the assisted breath (EAdi$_{assist}$) during an operation 1006 (operation of measuring EAdi during assisted breath). Again, it should be noted that it is within the scope of the present disclosure to use electrical activity of a respiratory muscle other than the patient's diaphragm.

As described in U.S. Pat. No. 5,820,560, the EAdi detector 905 may comprise an array of electrodes mounted on an esophageal catheter passing through the center of the patient's diaphragm depolarizing region. The position of the center of the patient's diaphragm depolarizing region is determined through detection of a reversal of polarity of the electromyographic component of the electrode-detected electromyographic signals. First and second electromyographic signals detected by the electrodes of the array on opposite sides of the patient's diaphragm depolarizing region are subtracted from each other, this subtraction cancelling the noise components of the first and second electromyographic signals but adding the respective electromyographic components of these first and second signals together to produce an electromyographic signal (EAdi) having an improved signal-to-noise ratio, having a reduced electrode-position-induced filter effect, and being representative of a demand to inspire from the patient's brain.

Figure 1:
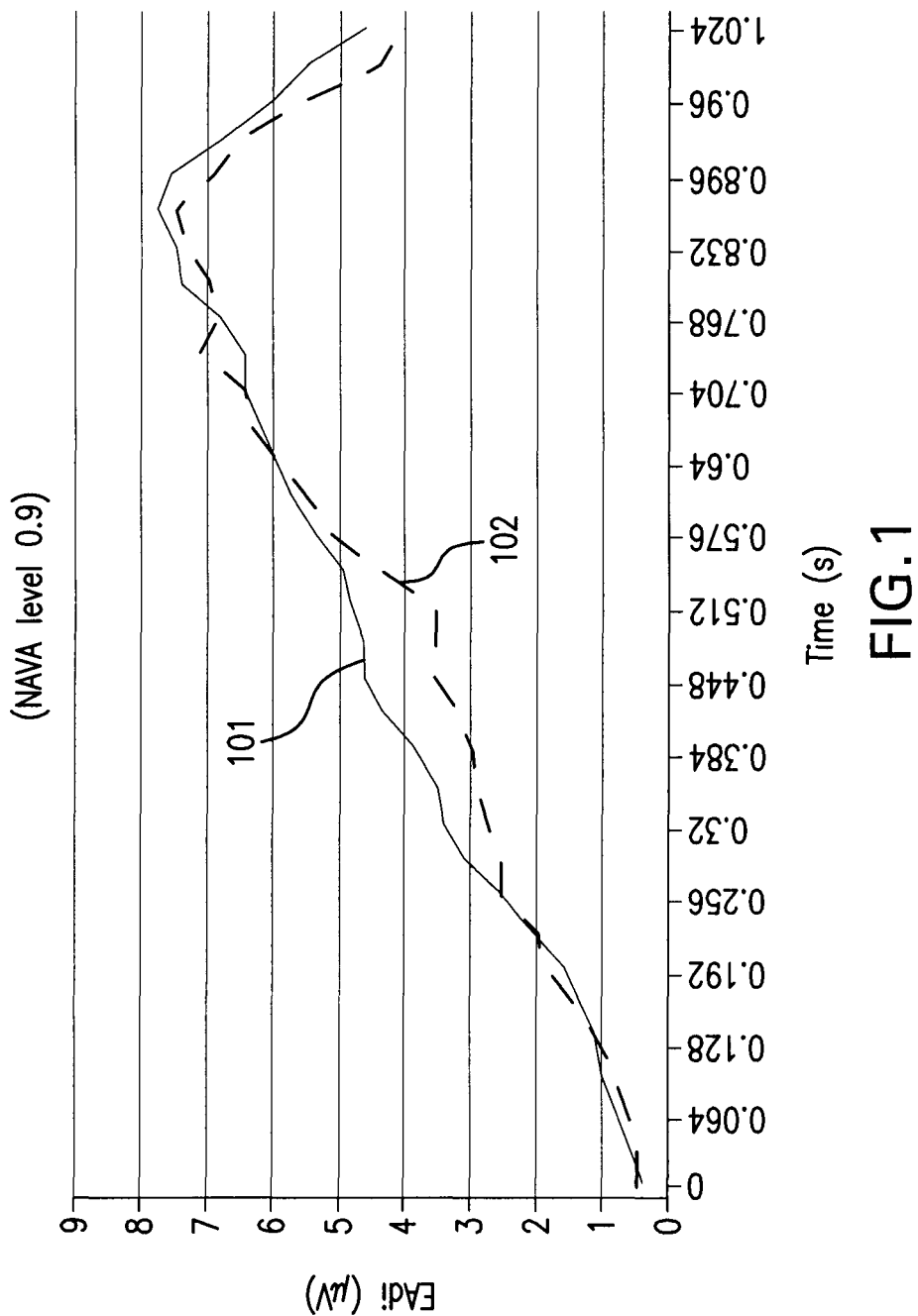
FIG. 1 is a graph showing a curve of electrical activity of a patient's diaphragm during a patient's inspiration with mechanical ventilatory assist (assisted breath) and a curve of electrical activity of the patient's diaphragm during a patient's inspiration without mechanical ventilatory assist (non-assisted breath)

FIG. 1 is a graph showing a curve 101 of an example of EAdi measured during a patient's inspiration with mechanical ventilatory assist referred to as "assisted breath", and a curve 102 of an example of EAdi measured during a subsequent patient's inspiration without mechanical ventilatory assist referred to as "non-assisted breath".

To simplify the model, assisted and non-assisted breaths with similar EAdi waveforms are presented in FIG. 1. Specifically, both the assisted and non-assisted breaths use the same neural recruitment and will, with the exception of some velocity of shortening and length-tension reductions of muscle function due to increases in flows and volumes during the assisted breath, provide a similar inspiratory muscle force generation.

During an operation 1007 of measuring patient's inspiratory volume during the non-assisted breath, a pneumatograph 907 (detector) measures the inspiratory volume V$_{no\text{-}assist}$ during the non-assisted breath. In the same manner, during an operation 1008 of measuring patient's inspiratory volume during the assisted breath, the pneumatograph 907 measures the inspiratory volume V$_{assist}$ during that non-assisted breath. It is within the scope of the present disclosure to implement at least one volume/flow detector other than a pneumatograph.

Figure 2:
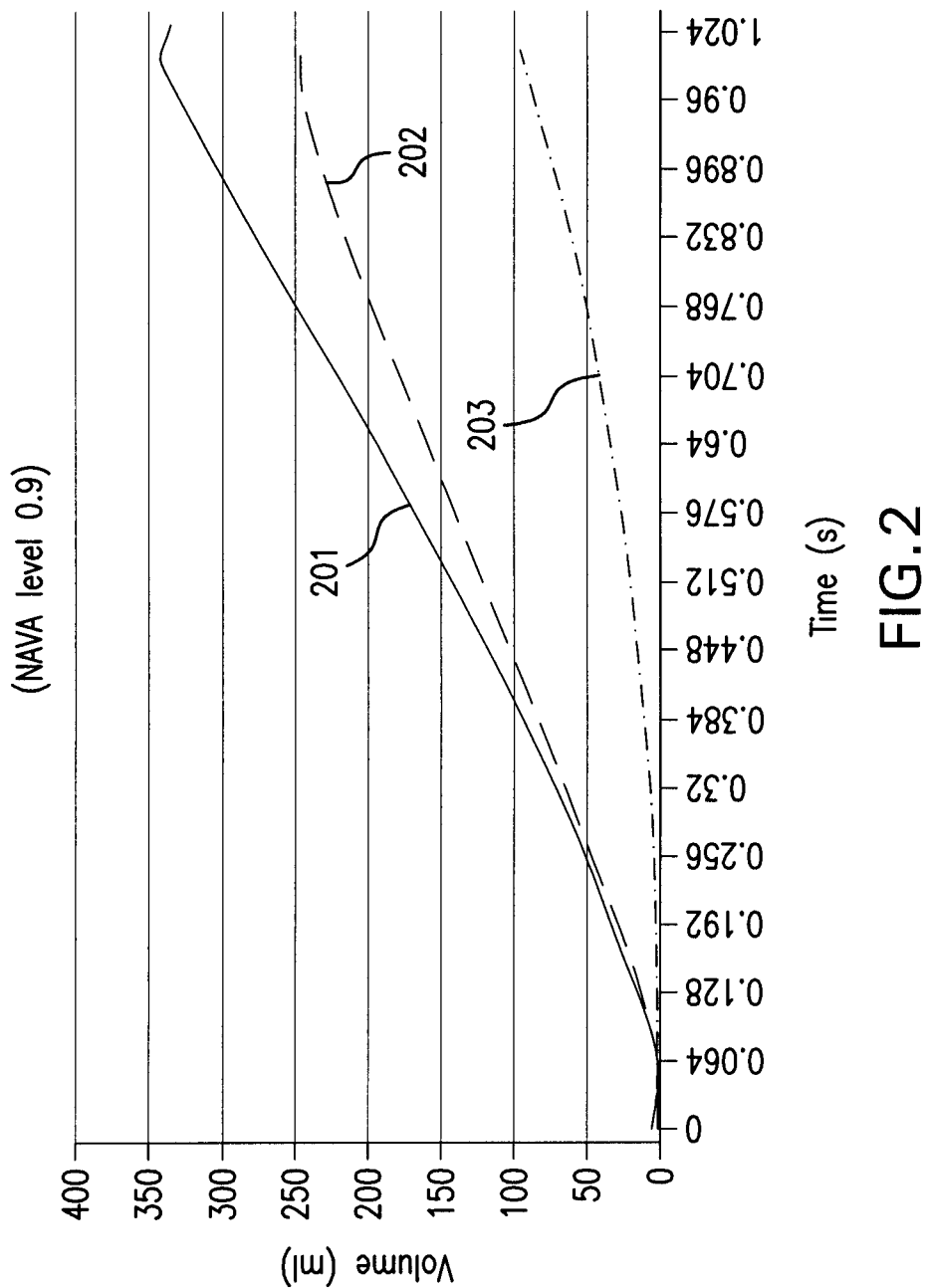
FIG. 2 is a graph showing a curve of an inspiratory volume generated by both the patient and the mechanical ventilator during assisted breath, a curve of an inspiratory volume generated by the patient only during a non-assisted breath, and a curve of a difference in inspiratory volume between the assisted and non-assisted breaths representing the contribution of the mechanical ventilator to inspiratory volume during assisted breath.

FIG. 2 is a graph showing a curve 201 of the patient's inspiratory volume V$_{assist}$ generated by both the patient and the mechanical ventilator measured during the patient's assisted breath, and a curve 202 of the inspiratory volume generated by the patient only, measured during the patient's non-assisted breath. The difference in inspiratory volume between the assisted and non-assisted breaths represents the contribution V$_{vent}$ of the mechanical ventilator 902 to inspiratory volume during the assisted breath (curve 203).

Since FIG. 1 shows two breaths with similar neural recruitment, one is assisted (curve 101) and a second is not assisted (curve 102), this functionally means that the inspiratory volume generated both by the patient and the mechanical ventilator and measured during the assisted breath (FIG. 2, curve 201) will be larger than the inspiratory volume generated by the patient only and measured during the non-assisted breath (FIG. 2, curve 202). Thus the difference in inspiratory volume between the assisted and non-assisted breaths calculated in operation 1009 by a subtractor 909 represents a contribution V$_{vent}$ of the mechanical ventilator 902 to patient's inspiratory volume (FIG. 2, curve 203):

$$V_{vent} = V_{assist} - V_{no\text{-}assist} \quad (1)$$

where V$_{vent}$ is the patient's inspiratory volume contributed by the mechanical ventilator 902, V$_{assist}$ is the patient's inspiratory volume generated by both the patient and the ventilator during the patient's assisted breath, and V$_{no\text{-}assist}$ is the patient's inspiratory volume generated by the patient only during the non-assisted breath.

In the same fashion, during an operation 1010 of measuring patient's inspiratory flow during the non-assisted breath, the pneumatograph 907 measures the inspiratory flow F$_{no\text{-}assist}$ during the non-assisted breath. In the same manner, during an operation 1011 of measuring patient's inspiratory flow during the assisted breath, the pneumatograph 907 measures the inspiratory flow F$_{assist}$ during the assisted breath.

The difference in inspiratory flow between the assisted and non-assisted breaths is calculated in operation 1012 by a subtractor 912. The difference in inspiratory flow during the assisted (F$_{assist}$) and non-assisted (F$_{no\text{-}assist}$) breaths provides information on the inspiratory flow F$_{vent}$ generated by the mechanical ventilator only:

$$F_{vent} = F_{assist} - F_{no\text{-}assist} \quad (2)$$

The inspiratory flow values F$_{vent}$, F$_{assist}$ and F$_{no\text{-}assist}$ may be used by the controller 904 to control inspiratory flow supplied by the mechanical ventilator 902 to the patient 901 in relation to the structure of the ventilatory assist mode being used.

It should be noted that all calculations are based on similar levels of EAdi amplitude during assisted and non-assisted breaths. If the levels of EAdi are not comparable compensation for inequalities in EAdi levels between assisted and non-assisted breaths is required. For example, the data stored for a number of non-assisted breaths can be used to determine and use a mean value of EAdi level.

Obtaining Respiratory System Pressure Vs Volume Curves, Respiratory System Mechanics, Patient's Relative Pressure Contribution Used for Inspiration During an operation 1013 of measuring the mechanical ventilatory assist pressure P$_{vent}$ delivered by the mechanical ventilator 902 to the patient 901, a pressure sensor 913 measures the mechanical ventilatory assist pressure P$_{vent}$. The pressure sensor 913 is normally integrated to the mechanical ventilator 902 but other types of implementation are possible. Examples of pressure sensors are diaphragm pressure sensors, differential pressure sensors, etc. As a non-limitative example, a diaphragm pressure sensor may comprise a metal diaphragm with piezoelectric gauges bonded thereon. The diaphragm is subjected to the pressure of the gas to be measured and the piezoelectric gauges sense the deformation in the metal of the diaphragm caused by the gas pressure to provide a measurement of that pressure. Of course, other types of pressure sensors can be implemented.

Figure 3:
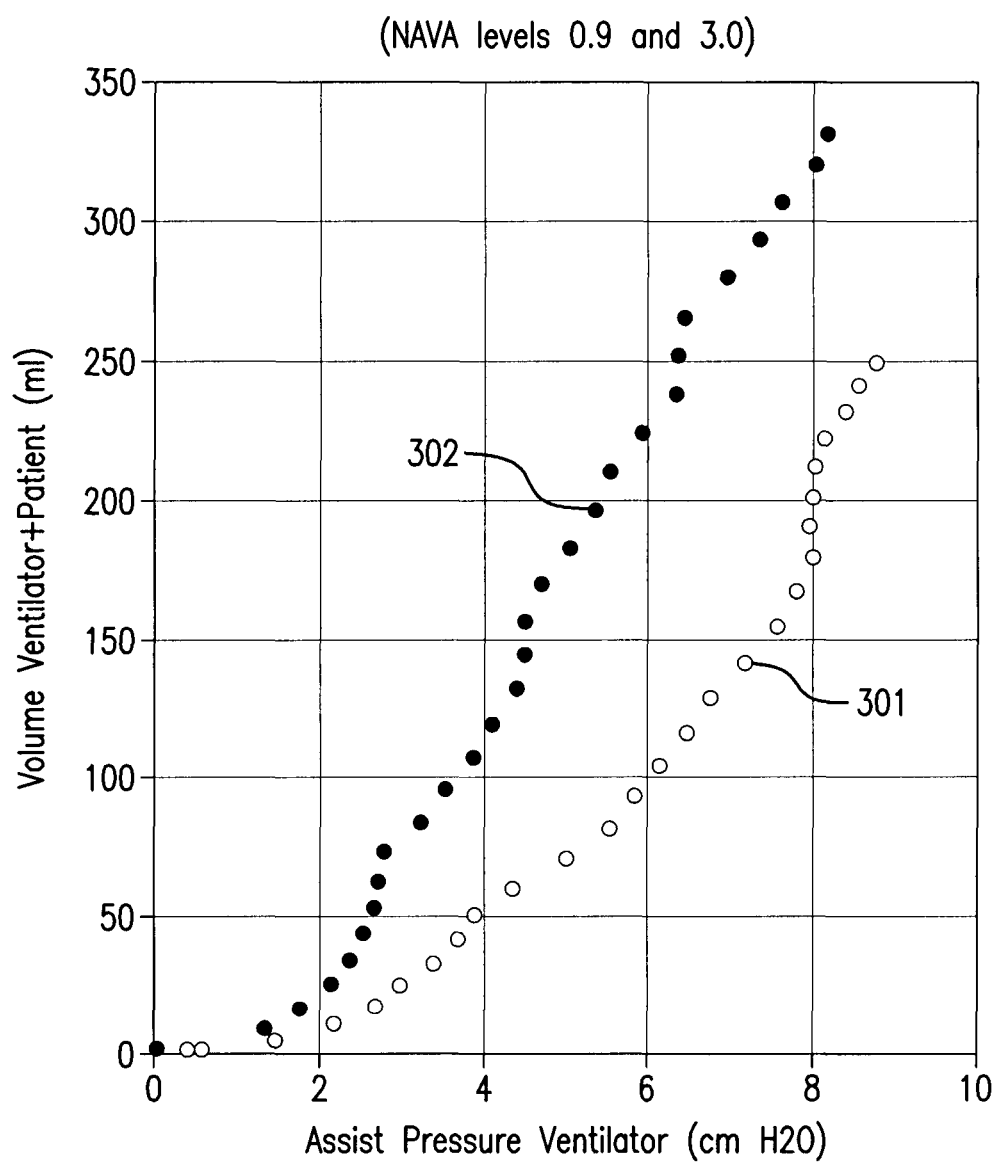
FIG. 3 is a graph of mechanical ventilatory assist pressure delivered by the ventilator ($P_{vent}$) on the x-axis and inspiratory volume generated by both the patient and the ventilator ($V_{assist}$) on the y-axis for patient's assisted breath, using proportional pressure assist with different gain levels.

During an operation 1014, a calculator 914 calculates a relation between the mechanical ventilatory assist pressure P$_{vent}$ and the inspiratory volume V$_{assist}$, for example by building a curve of the mechanical ventilatory assist pressure $P_{vent}$ versus the inspiratory volume $V_{assist}$. FIG. 3 is the graph of the mechanical ventilatory assist pressure $P_{vent}$ delivered by the mechanical ventilator on the x-axis and the inspiratory volume $V_{assist}$ generated by both the patient and the ventilator on the y-axis for two assisted breaths (inspirations), using proportional pressure assist with different gain levels. Curve 301 is related to a higher gain level (NAVA level of 3.0) and of curve 302 is related to a lower ($\frac{1}{3}^{rd}$) gain level (NAVA level of 0.9).

Figure 4:
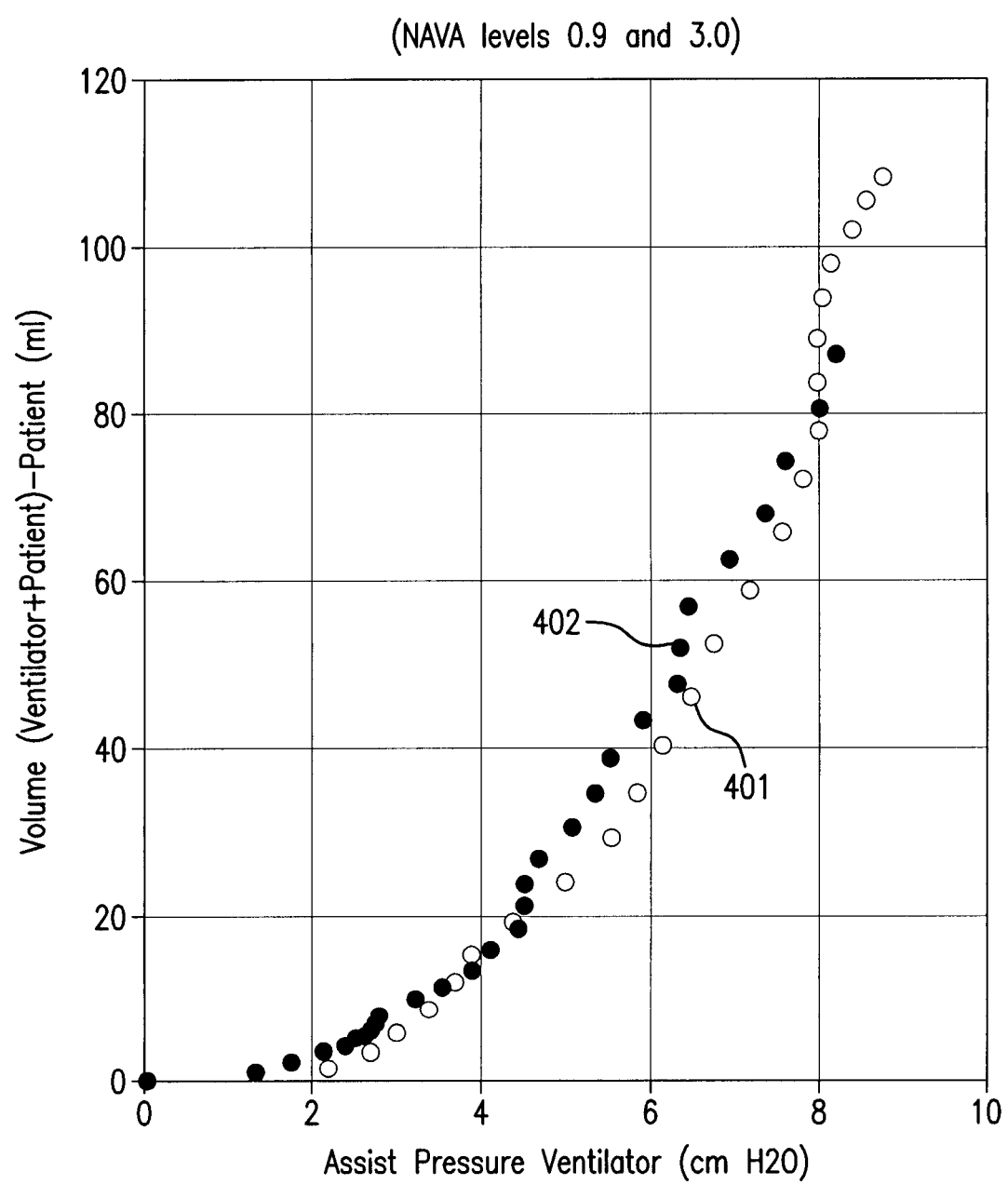
FIG. 4 is a graph showing the mechanical ventilatory assist pressure delivered by the mechanical ventilator ($P_{vent}$) on the x-axis and the inspiratory volume generated by the ventilator ($V_{vent}$), i.e. the inspiratory volume produced by both the ventilator and the patient ($V_{assist}$) minus the inspiratory volume generated by the patient alone ($V_{no-assist}$) on the y-axis for the same two assisted breaths (inspirations) as in FIG. 3, using proportional pressure assist with the same different gain levels as in FIG. 3.

During an operation 1015, a calculator 915 calculates a relation between the mechanical ventilatory assist pressure $P_{vent}$ and the inspiratory volume $V_{vent}$, for example by building a curve of the pressure $P_{vent}$ versus the inspiratory volume $V_{vent}$. FIG. 4 is the graph showing the mechanical ventilatory assist pressure $P_{vent}$ delivered by the mechanical ventilator on the x-axis and the inspiratory volume $V_{vent}$ generated by the ventilator, i.e. the inspiratory volume $V_{assist}$ produced by both the ventilator and the patient minus the inspiratory volume $V_{no-assist}$ generated by the patient alone on the y-axis for the same two assisted breaths (inspirations) as in FIG. 3, using proportional pressure assist with the same different gain levels (NAVA levels) as in FIG. 3. In FIG. 4, curve 401 is related to a higher gain level (NAVA level of 3.0) and curve 402 is related to a lower gain level (NAVA level of 0.9).

In FIG. 3, the two curves 301 and 302 are different since the patient's contribution to inspiratory pressure and volume is unknown. In FIG. 4 both curves 401 and 402 superimpose since the patient's pressure contribution is removed and the mechanical ventilator pressure contribution $P_{vent}$ is the only pressure overcoming the patient's respiratory system load to generate inspiratory volume.

Figure 5:
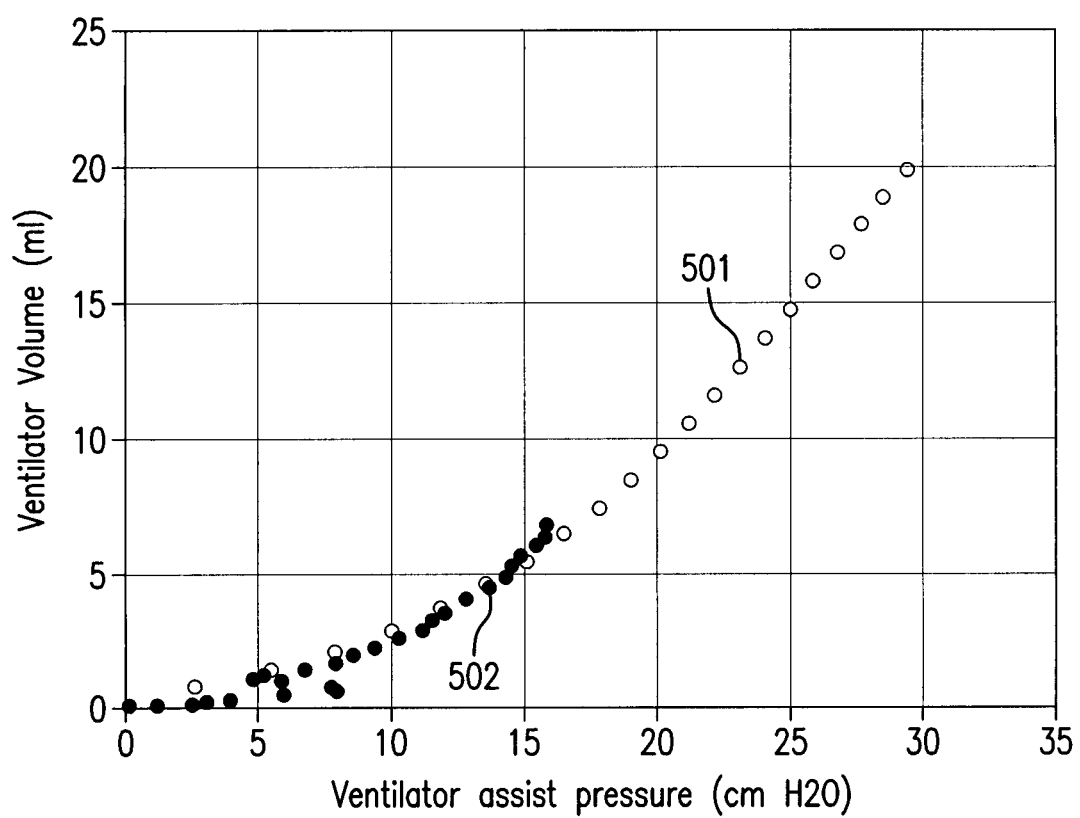
FIG. 5 is a graph including a first curve showing resulting ventilator pressure/volume relationship ($P_{vent}$ vs $V_{vent}$) obtained using a method similar to that depicted in FIGS. 1-4, and a second curve showing the pressure required for the respiratory system to obtain a given lung volume during respiratory muscle paralysis.

FIG. 5 shows experimental results in rabbits. Curve 502 shows the resulting ventilator pressure/volume relationship ($P_{vent}$ vs $V_{vent}$), obtained using a method similar to that depicted in FIG. 1-4. Specifically, curve 502 represents the pressure required for the patient's respiratory system to obtain a given patient's lung volume. As a reference, curve 501 defines a pressure/volume curve obtained during volume controlled ventilation after paralysis in the same experiment with same inspiratory flow as during spontaneous breathing.

As noted in FIG. 5, the subtraction of the inspiratory volume produced by the patient's inspiratory muscle defines a pressure/volume curve 502 ($P_{vent}$ vs $V_{vent}$) resembling in shape to the pressure/volume curve 501 of controlled mode ventilation during paralysis, thus a representation of the relaxed pressure/volume curve of the respiratory system.

Since the ventilatory assist level controlling device and method is based upon subtracting inspiratory volume $V_{no-assist}$ of a non-assisted breath from inspiratory volume $V_{assist}$ of an assisted breath, the resulting volume value will be reduced, e.g. $V_{vent}$ cannot reach end-inspiration volume, unless the ventilatory assist overcomes 100% of the patient's respiratory system load. The following description explains how to extend the pressure/volume curve and predict values for entire inspirations during partial ventilatory assist.

Increases in EAdi are proportional to increases in inspiratory muscle contraction, lung-distending pressure and lung volume, however with some influence on volume (chest-wall configuration) from the length-tension relation of the diaphragm. Inherent to its construction, patient's increase of EAdi with an EAdi-controlled proportional ventilatory assist system (or other system delivering pressure in proportion to inspiratory effort) increases proportionally both the patient's and the ventilator's pressure/force acting to inflate the lungs. Hence, increasing EAdi 1) increases both patient's and ventilator's respiratory system distending pressures/forces to generate volume and 2) changes patient's and ventilator's respiratory system distending pressures/forces proportionally.

Also, the ventilatory assist from a mechanical ventilator for any given level of EAdi (or other measurement of neural effort) can be changed by adjusting the gain determining the amount of ventilator-generated pressure a certain level of EAdi should generate, as described for example in U.S. Pat. No. 5,820,560. Using NAVA (Neurally Adjusted Ventilatory Assist), this adjustment of gain is performed by changing the so called NAVA level, as described for example in the article of Sinderby C., Navalesi P., Beck J., Skrobik Y. Comtois N., Friberg S., Gottfried S. B., Lindström L., "Neural Control of Mechanical Ventilation in Respiratory Failure", Nature Medicine, Vol. 5 (12): pp 1433-1436, December 1999, of which the full content is herein incorporated by reference. In contrast, patient's efficiency to generate lung distending pressure for a given EAdi cannot be adjusted, but may change according to patient's physiological or patho-physiological factors.

Due to human physiology and construction of proportional assist ventilation systems, increasing respiratory drive (e.g. EAdi) have similar effect on both patient's and ventilator's chest wall and lung distending pressures/forces, with different relative contribution depending on the patients neuro-mechanical efficiency (NME) and the gain setting used for proportional assist (e.g. the NAVA level). NME is defined as the efficiency of the patient's respiratory system to generate inspiratory pressure in response to electrical activity of the patient's diaphragm (EAdi).

From the above reasoning it follows that, throughout an entire inspiration, increasing (FIG. 3) positive pressure $P_{vent}$ generated by the proportional assist ventilator must be mirrored (proportional) by an increasing negative lung-distending pressure generated by the patient's respiratory muscles. Once the patient's volume contribution is subtracted (FIG. 4), it is possible to compare the ventilator's assist pressure $P_{vent}$ values at matching inspiratory volumes generated by the patient and the ventilator ($V_{assist}$, FIG. 6, curve 601) and ventilator alone ($V_{vent}$) i.e. patient-generated volumes subtracted (FIG. 6, curve 602).

Figure 6:
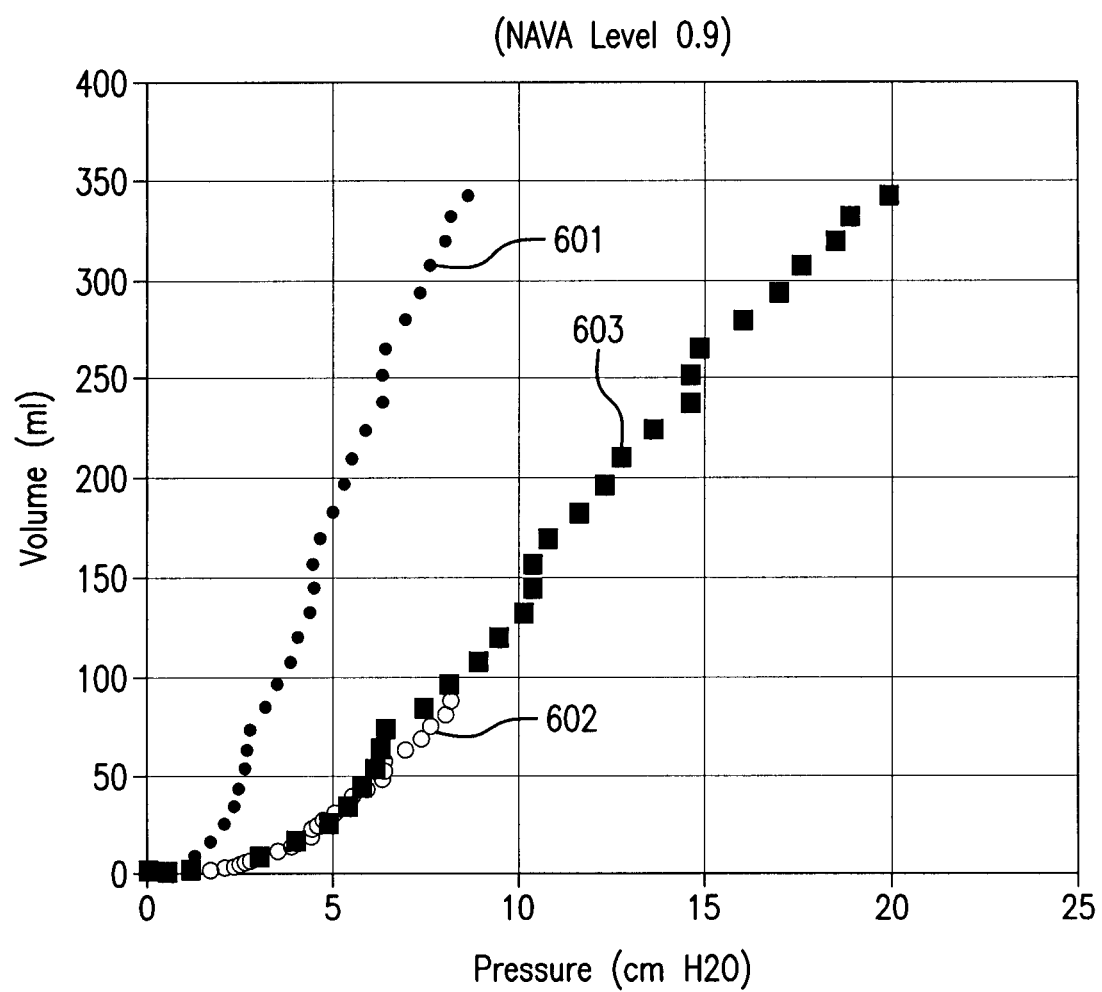
FIG. 6 is a graph including a curve of the ventilator's assist pressure versus volume generated by both the patient and the ventilator, a curve of the ventilator's assist pressure versus volume generated by the ventilator alone, and a curve of an extrapolated ventilator's assist pressure versus the volume generated by both the patient and the ventilator.

FIG. 6 is a graph showing the ventilator's assist pressure $P_{vent}$ on the x-axis versus volumes on the y-axis generated by both the patient and the ventilator ($V_{assist}$, curve 601) and the ventilator alone ($V_{vent}$, curve 602). Curve 603 shows the ventilator's assist pressure $P_{vent}$ adjusted to match the curve 602 of $V_{vent}$. This predicted extension (extrapolation) of $P_{vent}$ values reaching higher volumes $V_{vent}$ until end-inspiratory volume, is subsequently referred to as $P_{pred}$. The predicted pressure $P_{pred}$ can simply be calculated as follows.

In operation 1016, a calculator 916 determines a ratio between values of the ventilator's assist pressure $P_{vent}$ at same inspiratory volumes $V_{vent}$ and $V_{assist}$. Values of $P_{vent}$ (at volume $V_{assist}$) from curve 601 of FIG. 6 and of $P_{vent}$ (at volume $V_{vent}$) from FIG. 4 can be used. Specifically, the calculator 916 computes the ratio:

$$P_{vent}(V_{vent})/P_{vent}(V_{assist}) \text{ where } V_{vent}=V_{assist} \qquad (3)$$

From the example of FIG. 6, $P_{vent}$ at $V_{vent}$ (curve 603) of 84 ml (7.4 cmH$_2$O) divided by $P_{vent}$ at $V_{assist}$ (curve 601) of 84 ml (3.2 cmH$_2$O) equals a ratio of 2.3. The ratio of Equation (3) is calculated for a plurality of inspiratory volumes $V_{vent}$ and $V_{assist}$.

In an operation 1017, a multiplier 917 multiplies the values of $P_{vent}$ by the corresponding ratios of Equation (3) in order to calculate a relation between the predicted pressure $P_{pred}$ and the inspiratory volume $V_{assist}$, for example by building a curve of the predicted pressure $P_{pred}$ versus the inspiratory volume $V_{assist}$. When plotted against the inspiratory volume $V_{assist}$ (FIG. 6, curve 603), the predicted pressure $P_{Pred}$ provides a pressure/volume curve of the patient's respiratory system for the entire inspiration.

In an operation 1018 of calculating $P_{pred}$ at VT (VT=tidal volume), the curve 603 of FIG. 6 is used by a calculator 918 to determine the pressure assist required to generate the tidal volume VT, that is $P_{pred}$@VT. Tidal volume is the lung volume representing the normal volume of air displaced between normal inhalation and exhalation when extra effort is not applied; this tidal volume can be measured, for example, using the pneumatograph 907. Curve-fitting methods can be used for extrapolation to obtain pressure values at higher inspiratory volumes than those spontaneously generated by the patient.

The pressure required by the patient to generate the tidal volume, i.e. $P_{pred}$@VT, can be used by the controller 904 in any proportional or non-proportional ventilatory assist mode to determine the ratio or percentage of pressure assist being delivered in relation to the pressure being required.

As depicted in FIG. 6 the ratio/percentage of $P_{vent}$ to $P_{pred}$ can be obtained at any inspiratory volume $V_{assist}$. Consequently, in an operation 1019 of calculating a pressure $P_{pat-pred}$ generated by the patient, a subtractor 919 subtracts $P_{vent}$ from $P_{pred}$ at a same volume $V_{assist}$ to provide the pressure $P_{pat-pred}$ generated by the patient:

$$P_{pat-pred} = P_{pred} - P_{vent} \quad (4)$$

Then in an operation 1020 of calculating a patient's contribution $P_{pat}$% VT to inspiratory pressure in %, a calculator 920 solves the following Equation:

$$P_{pat}\% \, VT = (P_{pat-pred}/P_{vent}) \times 100 \quad (5)$$

Equation 5 may be calculated for $P_{pat-pred}$ and $P_{vent}$ at any inspiratory lung volume, including VT at end-inspiration ($P_{pat}$% VT).

The inspiratory flow values $P_{pat-pred}$ and $P_{pat}$% VT may be used by the controller 904 to control inspiratory pressure applied by the mechanical ventilator 902 to the patient 901 in relation to the structure of the ventilatory assist mode being used.

The $P_{vent}$ versus $V_{vent}$ curve 602 and the $P_{pred}$ versus $V_{assist}$ curve 603 of FIG. 6 show the pressures required to expand the entire respiratory system to a lower volume or throughout over the entire assisted inspiration, respectively. The end-inspiratory part of the curve (flow near zero) describes dynamic compliance (expressed for example as ml/cmH$_2$O) or elastance (described for example as cmH$_2$O/ml) of the total respiratory system. An actual $P_{pred}$ versus $V_{vent}$ curve will allow for calculation of respiratory system mechanics within the breath. Methods to calculate compliance or elastance from inspiratory pressure/volume curves are numerous and well described in the literature. Depending on the intended application, positive end-expiratory pressure (PEEP) can be included or subtracted.

Having the inspiratory flow $F_{vent}$ and predicted pressure $P_{pred}$ generated by the mechanical ventilator at different inspiratory volumes $V_{vent}$ it is possible to calculate the inspiratory airflow resistance (e.g. described as cm H$_2$O/ml/s). Methods to calculate resistance from continuous recordings of inspiratory pressure, flow and volume are also numerous and described in the literature.

Again, values of such dynamic compliance or elastance of the total respiratory system and inspiratory airflow resistance may be used by the controller 904 to control ventilatory assist supplied by the mechanical ventilator 902 to the patient 901 in relation to the structure of the ventilatory assist mode being used.

Obtaining EAdi in Relation to EAdi Required at Unassisted Tidal Volume

As described herein above EAdi$_{assist}$ is measured, in operation 1006, during a first breath with ventilatory assist and EAdi$_{no-assist}$ is measured, in operation 1005, during a second breath with no ventilatory assist. EAdi trajectories are similar for both breaths as shown in FIG. 1. The above described measurements of inspiratory volume $V_{assist}$ for patient+ventilator contribution during the first assisted breath (operation 1008) and of inspiratory volume $V_{no-assist}$ for patient alone during the second non-assisted breath (operation 1007) are also available.

Figure 7:
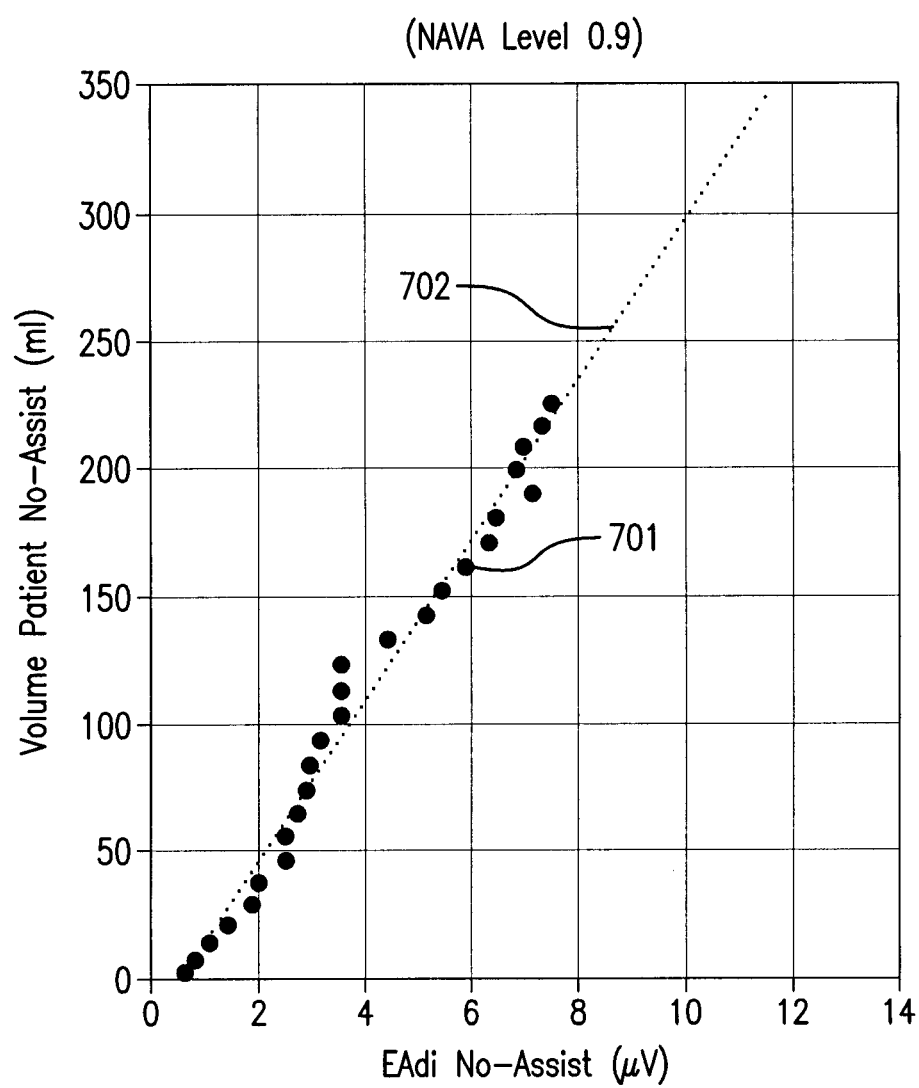
FIG. 7 is a graph showing a curve of patient's inspiratory volume for a breath with no assist (y-axis) versus patient's diaphragm electrical activity EAdi for the breath with no assist (x-axis)

In an operation 1021, the diaphragm electrical activity EAdi$_{pred}$@VT required by the patient to generate the tidal volume VT is determined by a calculator 921. FIG. 7 is a graph showing a curve 701 of the inspiratory volume $V_{no-assist}$ for a patient's breath with no ventilatory assist (y-axis) versus the diaphragm electrical activity EAdi$_{no-assist}$ for a breath with no assist (x-axis). Specifically, curve 701 represents the patient's inspiratory volume $V_{no-assist}$ generated for a given patient's diaphragm electrical activity EAdi$_{no-assist}$ during a non-assisted breath. Curve 701 makes it possible to estimate EAdi$_{no-assist}$ at any inspiratory lung volume $V_{no-assist}$ with no ventilatory assist. However, EAdi is anticipated to be similar during both assisted and non-assisted inspirations, and differences in inspiratory volumes at a given EAdi between assisted and non-assisted breaths are anticipated to decrease when NAVA levels are increased. In case of large volume differences between assisted and non-assisted breaths, curve fitting methods (dotted line 702 in FIG. 7) makes it possible to extrapolate the EAdi to obtain EAdi$_{pred}$@VT required for the non-assisted inspiratory volume $V_{no-assist}$ to reach VT, i.e. the inspiratory volume as observed in curve 603 of FIG. 6 or higher volumes, which would provide the estimated EAdi required for reaching the assisted inspiratory volume (equal to VT) without ventilatory assist.

In operation 1022, a calculator 922 uses EAdi$_{pred}$@VT required by the patient to generate the tidal volume VT and EAdi$_{no-assist}$ to calculate a percentage EAdi % VT of the electrical activity EAdi$_{no-assist}$ developed by the patient's respiratory muscle in relation to the predicted electrical activity EAdi$_{pred}$@VT required for the patient's respiratory muscle to produce the tidal volume, using Equation (6):

$$\text{EAdi \% } VT = (\text{EAdi}_{no-assist}/\text{EAdi}_{pred}@VT) \times 100 \quad (6)$$

Indeed, the EAdi$_{pred}$@VT required by the patient to generate the tidal volume VT can be used for any proportional or non-proportional assist mode to determine the ratio or percentage of electrical activity EAdi developed in relation to that EAdi$_{pred}$@VT required for producing the tidal inspiration (VT). For example, using FIG. 7, EAdi$_{no-assist}$ is about 8 µV and EAdi$_{pred}$@VT is about 12 µV (EAdi % VT=67%) suggesting that the patient develops about % of the electrical activity EAdi required to make the inspiration without assist.

Determining the Required Neuro-Mechanical Effort to Reach Inspiratory Volume

In operation 1023, neuromechanical efficiency of the patient's respiratory system (NMERS) is determined by a calculator 923.

By obtaining values of the predicted pressure $P_{pred}$ as shown, for example, in curve 603 of FIG. 6 and values of the electrical activity EAdi$_{no-assist}$ as shown, for example, by curve 701 of FIG. 7 at matching inspiratory lung volumes it is possible to calculate the ratio of $P_{pred}/EAdi_{no\text{-}assist}$ in $cmH_2O/\mu V$. Using $V_{vent}$ it is also possible to calculate this ratio using $P_{vent}$ at a given $V_{vent}$ and $EAdi_{no\text{-}assist}$ at the same value of $V_{no\text{-}assist}$. This ratio describes the amount of pressure required per unit EAdi to overcome the total respiratory system load, i.e. the neuromechanical efficiency of the patient's respiratory system (NMERS).

For example, at a lung volume of 200 ml, $P_{pred}$=12.3 $cmH_2O$ (FIG. 6, curve 603) and $EAdi_{no\text{-}assist}$=7.8 µV (FIG. 7, curve 701), providing a neuro-mechanical efficiency $NMERS_{no\text{-}assist}$ of the patient's respiratory system with no ventilatory assist of 1.6 $cmH_2O/\mu V$. This means that a tidal volume ($V_{assist}$) of 350 ml required a pressure $P_{pred}$@VT of 20 $cmH_2O$ (FIG. 6, curve 603) which in turn would require an $EAdi_{pred}$@VT of 12.5 µV (FIG. 7, curve 702). This is expressed in the following Equation:

$$P_{pred}@VT/NMERS_{no\text{-}assist}=EAdi_{pred}@VT \quad (7)$$

$$NMERS_{no\text{-}assist}=P_{pred}@VT/EAdi_{pred}@VT \quad (8)$$

With $P_{pred}$@VT=20 $cmH_2O$ and $NMERS_{no\text{-}assist}$=1.6 $cmH_2O/\mu V$, Equation (7) gives $EAdi_{pred}$@VT=12.5 µV. This is similar to extrapolated value for $EAdi_{pred}$@VT in FIG. 7, curve 702.

Figure 8:
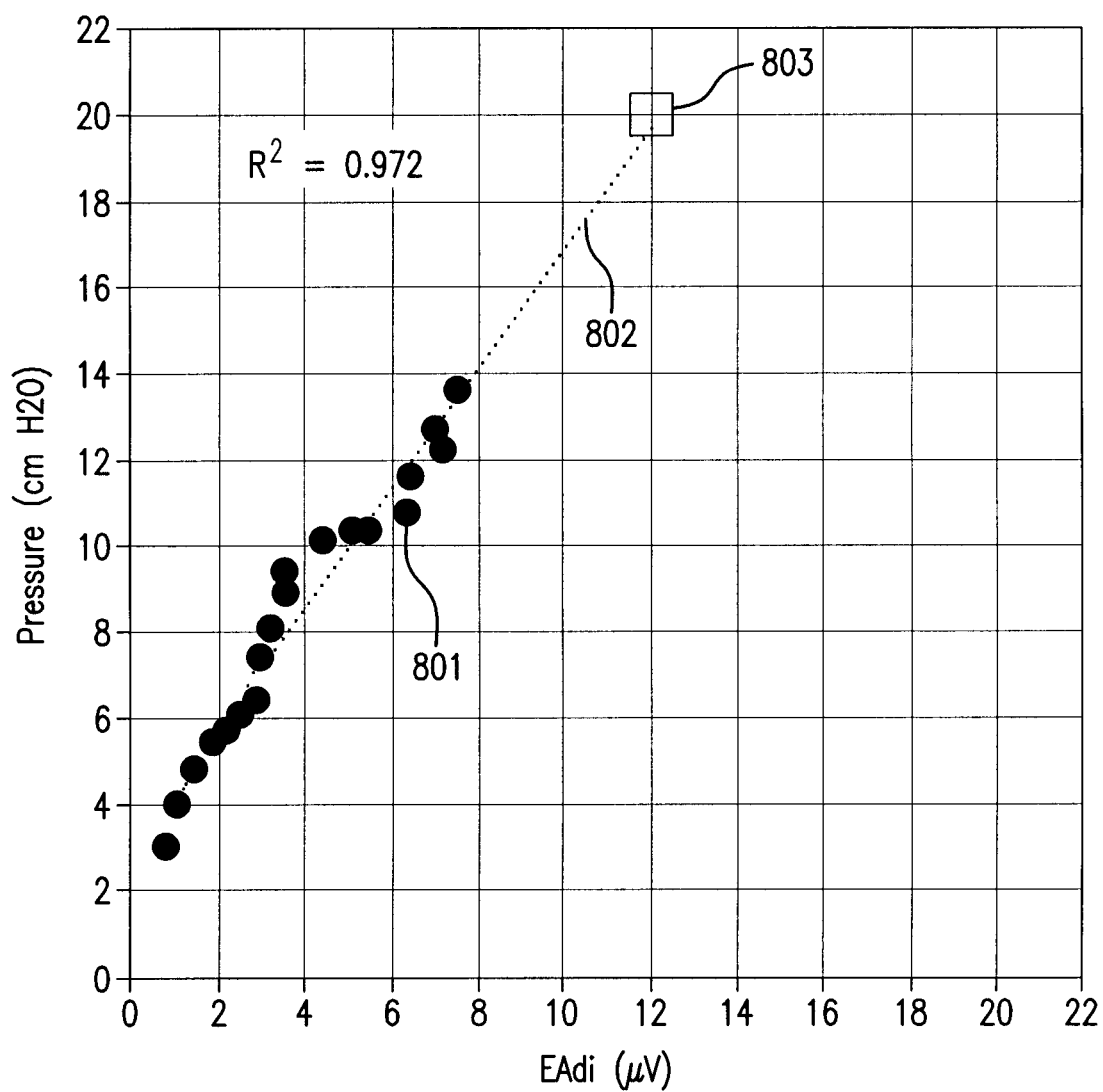
FIG. 8 is a graph showing a curve of $P_{pred}$ (y-axis) vs $EAdi_{no-assist}$ (X-axis) at matching inspiratory volumes.

FIG. 8, curve 801, shows the relationship of $P_{pred}$ (y-axis) versus $EAdi_{no\text{-}assist}$ (x-axis) at matching inspiratory volumes. Open square 803 shows $P_{pred}$@VT (y-axis) versus $EAdi_{pred}$@VT (x-axis). Dotted line 802 indicates a curve-fit model (in this case 2nd order polynomial) which makes it possible to obtain a mathematical function to correct for eventual nonlinearity.

Methods to Determine (Gain) Assist Levels

A gain factor for proportional assist, i.e. a NAVA level expressed, for example, in $cmH_2O/\mu V$, is required to deliver ventilatory assist and its impact can be calculated using the neuromechanical efficiency $NMERS_{no\text{-}assist}$. For example, applying a NAVA level that matches $NMERS_{no\text{-}assist}$ would double the inspiratory pressure generation for a given EAdi. For example, applying a NAVA level of 2 $cmH_2O/\mu V$ to a patient with a $NMERS_{no\text{-}assist}$ of 2 $cmH_2O/\mu V$ would add up a total of 4 $cmH_2O/\mu V$ to the neuromechanical efficiency with ventilatory assist $NMERS_{assist}$. In operation 1024, a calculator 924 computes the neuromechanical efficiency $NMERS_{assist}$:

$$NMERS_{assist}=NAVA\ level+NMERS_{no\text{-}assist} \quad (9)$$

After some breaths, this should reduce the EAdi required (and the inspiratory pressure generated by the patient) to generate the required volume to about half (if inspiratory volume remains unchanged).

In operation 1025, a calculator 925 computes the ratios $NMERS_{no\text{-}assist}/NMERS_{assist}$ and $NMERS_{assist}/NMERS_{no\text{-}assist}$.

The ratio $NMERS_{no\text{-}assist}/NMERS_{assist}$ (in %) indicates the percentage of reduction of EAdi with increasing NAVA levels from breathing without assist (NAVA level=0 $cmH_2O/\mu V$).

Conversely, the ratio $NMERS_{assist}/NMERS_{no\text{-}assist}$ indicates the fold increase in EAdi that can be expected when removing ventilatory assist i.e. returning the NAVA level to 0 $cmH_2O/\mu V$. Specifically, at a given NAVA level, the electrical activity EAdi at end-inspiration for a non-assisted breath times the ratio $NMERS_{assist}/NMERS_{no\text{-}assist}$ provides $EAdi_{pred}$@VT.

It is therefore possible to predict how changes in NAVA levels change the EAdi in terms of both absolute (µV) and relative (%) values.

FIG. 7 suggests that $EAdi_{pred}$@VT is about 12.5 µV whereas the observed EAdi during a non-assisted breath with a NAVA level of 0.9 is about 8 µV. $NMERS_{no\text{-}assist}$ was found to be 1.6 $cmH_2O/\mu V$ (see above example), providing a $NMERS_{assist}$ Of 2.5 $cmH2O/\mu V$ ($NMERS_{no\text{-}assist}/NMERSa_{ssist}$=1.6/2.5=0.64). An EAdi pred @VT of 12.5 µV times a ratio $NMERS_{no\text{-}assist}/NMERSa_{ssist}$ 0.64 gives an EAdi of 8.0 µV.

According to FIG. 7, an EAdi of 7.7 µV results in a volume of about 230 ml.

Obviously, the above relations and calculated values can be used by the controller 904 to control the mechanical ventilator 902 and, accordingly, the variables of the patient's ventilatory assist.

Initial Setting of the NAVA Gain Level

In the case that the patient receives no assist, i.e. the patient is not receiving ventilatory support, an initial arbitrary NAVA level providing, for example, 10-20 $cmH_2O$ pressure delivered by the ventilator is used. Simple computation indicates that an EAdi of 20 µV with a NAVA level of 1 should target 20 $cmH_2O$ in peak pressure. If assist is sufficient this should be due to unloading; then a) increase inspiratory volume and/or b) reduce EAdi.

If the patient is ventilated with an assist mode other than NAVA, existing and built in tools can be used for transferring the patient to a NAVA ventilatory assist mode. If EAdi is clearly above noise level, it is possible to estimate ventilator's assist pressure to inspiratory EAdi ($cmH_2O/\mu V$) related to the ventilatory assist mode being applied and use this value as the initial NAVA level.

Examples of Simplified Applications

The method and system provided above can be modified to fit any other modes of mechanical ventilation even when such modes cannot deliver proportional pressure ventilatory assist.

Comparison of inspiratory volumes between assisted and non-assisted breaths using only the inspiratory volume and EAdi at one point e.g. at peak EAdi or peak volume or at matching EAdi or volume or any combination of these can be used by the controller 904 to control the mechanical ventilator 902. For example a breath with ventilatory assist gives a $V_{assist}$ of 400 ml for an EAdi of 10 µV and a breath with no assist gives a $V_{no\text{-}assist}$ of 200 ml for an EAdi of 10 µV. Measured ventilator's pressure $P_{vent}$ for the assisted inspiration is equal to 10 $cmH_2O$. Subtracting inspiratory volume of non-assisted breath from inspiratory volume of assisted breath (400 ml–200 ml) leaves a volume of 200 ml for the ventilator to deliver at matching EAdi at pressure of 10 $cmH_2O$. In this example, volume to pressure ratio for the patient's respiratory system ($P_{RS}$) is 20 $ml/cmH_2O$ and requires 10 µV.

Simply assuming that breaths following each other have similar respiratory drive (similar EAdi levels) it is possible to just subtract the inspiratory volumes of the non-assisted breaths from those of the assisted breaths and divide the result by the ventilatory assist pressure above PEEP.

In this respect, it should be noted that if peak EAdi difference as shown in FIG. 1 between non-assisted and assisted breaths is small, for example lower or equal to 20%, the ventilatory assist level controlling method 1000 is performed. However, if peak EAdi difference between non-assisted and assisted breaths is higher than 20%, data are disregarded and calculations are aborted.

Example of Control of the Mechanical Ventilator

In this example, a target $P_{pat}\%\ VT_{target}$ is inputted to the controller 904 (FIGS. 9 and 10). The controller 904 then compares the patient's contribution $P_{pat}\%\ VT$ to inspiratory pressure from calculator 920 to this input target $P_{pat}\%\ VT_{target}$. If patient's contribution $P_{pat}\%\ VT$ is equal to or larger than target $P_{pat}\%\ VT_{target}$, the assist i.e. the NAVA level is increased. If patient's contribution $P_{pat}\%\ VT$ is lower than target $P_{pat}\%\ VT_{target}$, the assist i.e. the NAVA level is decreased. Increase and decrease of the NAVA level can be made by predetermined increments and decrements.

After inputting the target $P_{pat}\%\ VT_{target}$ to the controller 904, a new NAVA level is first calculated from the total pressure required to reach tidal volume VT using the predicted inspiratory pressure $P_{pred}@VT$ from calculator 918 and the patient's pressure contribution $P_{pat-pred}$ from subtractor 919 giving the patient's contribution $P_{pat}\%\ VT$ to the inspiratory pressure at tidal volume VT from calculator 920. These measurements are related to $EAdi_{pred}@VT$ from calculator 921 and EAdi % VT from calculator 922. Using these values, the neuro mechanical efficiency without assist $NMERS_{no-assist}$ and the neuro mechanical efficiency with assist $NMERS_{assist}$ are calculated.

The following is a numerical example of computations that may be performed by the controller 904. For example, if $P_{pat}\%\ VT$ is 50% and $P_{pred}@VT$ is 30 $cmH_2O$, $P_{pat-pred}$ is 15 $cmH_2O$. If, in this example, $EAdi_{pred}@VT$ is 10 µV, $NMERS_{assist}$ can be estimated to 30 $cmH_2O$/10 µV which is twice the $NMERS_{no-assist}$ due to the 50% value of the $P_{pat}\%\ VT_{target}$ inputted to the controller 904. The NAVA level equals $NMERS_{assist}$ minus $NMERS_{no-assist}$, i.e. the NAVA level equals $(30\ cm\ H_2O/10\ \mu V - 15\ cm\ H_2O/10\ \mu V))/10 = 1.5\ cmH_2O/\mu V$, where division by 10 represents division by $EAdi_{pred}@VT$. The controller 904 then monitor and analyze the signals $P_{pat}\%\ VT$ from calculator 921, EAdi % VT from calculator 922 and the ratio $NMERS_{assist}/NMERS_{no-assist}$ from calculator 925 to validate such value of the NAVA level, for example by determining whether these signals have expected values or ranges of values, otherwise the ventilator will trigger an alarm. In particular, if $P_{pat}\%\ VT$ is different from target $P_{pat}\%\ VT_{target}$, the NAVA level is modified as described above until target $P_{pat}\%\ VT_{target}$ is reached.

If subsequently, to help the patient to become capable of breathing on his own, $P_{pat}\%\ VT_{target}$ is set to 75% and $P_{pred}@VT$ is still 30 $cmH_2O$, $P_{pat-pred}$ is then 22.5 $cmH_2O$. In this example, the $EAdi_{pred}@VT$ is still 10 µV. The $NMERS_{assist}$ is then 30 $cmH_2O/10\ \mu V$ which is 1.33 times the neuromechanical efficiency $NMERS_{no-assist}$. $NMERS_{assist}$ is then 30 $cmH_2O/10\ \mu V$ and the NAVA level equals $NMERS_{assist}$ minus $NMERS_{no-assist}$, i.e. $((30\ cmH_2O/10\ \mu V) - (22.5\ cmH_2O/10\ \mu V))/10 = 0.75\ cmH_2O/\mu V$, the division by 10 represents division by $EAdi_{pred}@VT$.

The controller 904 continues to monitor and analyze the signals $P_{pat}\%\ VT$ from calculator 921, EAdi % VT from calculator 922 and the ratio $NMERS_{assist}/NMERS_{no-assist}$ from calculator 925, for example by determining whether these signals have expected values or ranges of values, otherwise the ventilator will trigger an alarm. Again, if $P_{pat}\%\ VT$ is different from target $P_{pat}\%\ VT_{target}$, the NAVA level is modified as described above until target $P_{pat}\%\ VT_{target}$ is reached. Also, the values of these signals will show whether the patient is capable of withstanding and adapting to this lower value (0.75) of the NAVA level and how close the patient is to be capable of breathing on his own.

Of course, it is within the scope of the present invention to use, in the controller 904 other types of control or ventilatory assist mode of the mechanical ventilator 902 using any values measured and calculated according to the present disclosure.

Figure 11:
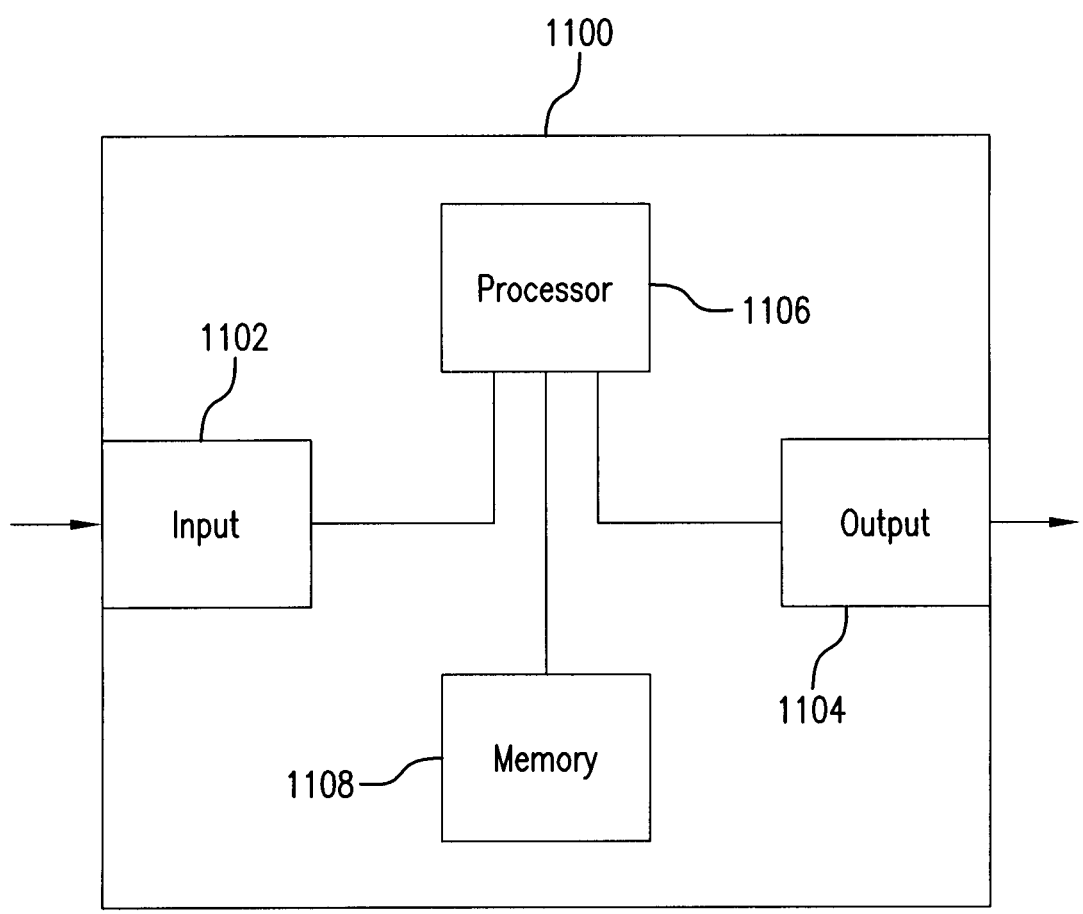
FIG. 11 is a simplified block diagram of an example configuration of hardware components forming the ventilatory assist level controlling method and device.

FIG. 11 is a simplified block diagram of an example configuration of hardware components forming the above described ventilatory assist level controlling device and method.

The ventilatory assist level controlling device and method (identified as 1100 in FIG. 11) comprises an input 1102, an output 1104, a processor 1106 and a memory 1108.

The input 1102 is configured to receive the EAdi, ventilator's pressure, inspiratory volume, and inspiratory flow measurements. The output 1104 is configured to supply the above described calculated data usable by the controller 904 to control the mechanical ventilator 902. The input 1102 and the output 1104 may be implemented in a common module, for example a serial input/output device.

The processor 1106 is operatively connected to the input 1102, to the output 1104, and to the memory 1108. The processor 1106 is realized as one or more processors for executing code instructions in support of the functions of the various modules of the ventilatory assist level controlling device and method as shown in FIGS. 9 and 10.

The memory 1108 may comprise a non-transient memory for storing code instructions executable by the processor 1106, specifically, a processor-readable memory comprising non-transitory instructions that, when executed, cause a processor to implement the modules of the ventilatory assist level controlling device 900 (FIG. 9) and the operations of the ventilatory assist level controlling method 1000 (FIG. 10) as described in the present disclosure. The memory 1108 may also comprise a random access memory or buffer(s) to store intermediate processing data from the various functions performed by the processor 1106.

Those of ordinary skill in the art will realize that the description of the ventilatory assist level controlling device and method are illustrative only and are not intended to be in any way limiting. Other embodiments will readily suggest themselves to such persons with ordinary skill in the art having the benefit of the present disclosure. Furthermore, the disclosed device and method may be customized to offer valuable solutions to existing needs and problems of controlling mechanical ventilatory assist.

In the interest of clarity, not all of the routine features of the implementations of the ventilatory assist level controlling device and method are shown and described. It will, of course, be appreciated that in the development of any such actual implementation of the device and method, numerous implementation-specific decisions may need to be made in order to achieve the developer's specific goals, such as compliance with application-, system-, network- and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of controlling mechanical ventilatory assist.

In accordance with the present disclosure, the modules, processing operations, and/or data structures described herein may be implemented using various types of operating systems, computing platforms, network devices, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used. Where a method comprising a series of operations is implemented by a processor, computer or a machine and those operations may be stored as a series of non-transitory code instructions readable by the processor, computer or machine, they may be stored on a tangible and/or non-transient medium.

Modules of the ventilatory assist level controlling device and method as described herein may comprise software, firmware, hardware, or any combination(s) of software, firmware, or hardware suitable for the purposes described herein.

In the ventilatory assist level controlling method as described herein, the various operations may be performed in various orders and some of the operations may be optional.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A method for controlling a level of ventilatory assist applied to a patient by a mechanical ventilator, comprising:
    determining, for each of a plurality of assisted breaths of the patient:
        a total measured inspiratory volume, wherein the total measured inspiratory volume is produced by both the patient and the mechanical ventilator,
        a difference measured inspiratory volume, wherein the difference measured inspiratory volume is contributed by the mechanical ventilator, and
        a measured inspiratory assist pressure produced by the mechanical ventilator;
    calculating a first relation between inspiratory assist pressure values $P_{vent}$ and total inspiratory volume values $V_{assist}$ by building a first curve in which each point corresponds to one of the measured inspiratory assist pressures and to a corresponding one of the total measured inspiratory volumes;
    calculating a second relation between the inspiratory assist pressure values $P_{vent}$ and difference inspiratory volume values $V_{vent}$ by building a second curve in which each point corresponds to one of the measured inspiratory assist pressures and to a corresponding one of the difference inspiratory volumes;
    using a plurality of points of the first curve and a corresponding plurality of points of the second curve, calculating a plurality of ratios between (i) inspiratory assist pressure values $P_{vent}$ of the second curve at respective difference inspiratory volume values $V_{vent}$ of the second curve and (ii) inspiratory assist pressure values $P_{vent}$ of the first curve at respective total inspiratory volume values $V_{assist}$ of the first curve, wherein the plurality of points of the first curve and the plurality of points of the second curve are selected so that each ratio is calculated using equal values for the total inspiratory volume value $V_{assist}$ and for the difference inspiratory volume value $V_{vent}$;
    for each point of the first curve, multiplying the measured inspiratory assist pressure by the ratio corresponding to the total measured inspiratory volume to calculate a third relation between predicted inspiratory pressure values $P_{pred}$ and the total inspiratory volume values $V_{assist}$; and
    controlling the mechanical ventilator using the third relation to control the level of ventilatory assist.

2. The ventilatory assist level controlling method as defined in claim 1, comprising:
    measuring electrical activity $EAdi_{no\text{-}assist}$ of a respiratory muscle during non-assisted breaths of the patient, and
    measuring electrical activity $EAdi_{assist}$ of the respiratory muscle during the assisted breaths of the patient.

3. The ventilatory assist level controlling method as defined in claim 2, wherein the respiratory muscle is the diaphragm of the patient.

4. The ventilatory assist level controlling method as defined in claim 1, comprising:
    determining the predicted inspiratory pressure $P_{pred}$ at a tidal volume of the patient using the third relation.

5. The ventilatory assist level controlling method as defined in claim 1, comprising:
    subtracting the measured inspiratory assist pressure at a given total inspiratory volume value $V_{assist}$ from the predicted inspiratory pressure value $P_{pred}$ at the given total inspiratory volume value $V_{assist}$ to obtain an inspiratory pressure value $P_{pat\text{-}pred}$ contributed by the patient.

6. The ventilatory assist level controlling method as defined in claim 5, comprising:
    calculating, at a tidal volume of the patient, a contribution of the patient $P_{pat}\% \, VT$ to inspiratory pressure using the following relation:

$$P_{pat}\% \, VT = (P_{pat\text{-}pred}/P_{vent}) \times 100.$$

7. The ventilatory assist level controlling method as defined in claim 2, comprising:
    calculating a predicted electrical activity $EAdi_{pred}@VT$ of the respiratory muscle required by the patient to generate a tidal volume using an extrapolating, curve-fitting technique applied to a curve of the electrical activity $EAdi_{no\text{-}assist}$ versus the inspiratory volume $V_{no\text{-}assist}$.

8. The ventilatory assist level controlling method as defined in claim 7, comprising:
    calculating a percentage $EAdi \% \, VT$ of the electrical activity $EAdi_{no\text{-}assist}$ developed by a respiratory muscle of the patient in relation to the predicted electrical activity $EAdi_{pred}@VT$ required for the respiratory muscle of the patient to produce the tidal volume, using the relation:

$$EAdi \% \, VT = (EAdi_{no\text{-}assist}/EAdi_{pred}@VT) \times 100.$$

9. The ventilator assist level controlling method as defined in claim 7, comprising:
    determining a predicted pressure $P_{pred}@VT$ at a tidal volume of the patient VT using the third relation; and
    calculating a neuromechanical efficiency of a respiratory system of the patient $NMERS_{no\text{-}assist}$ for the non-assisted breath of the patient as a function of the predicted pressure $P_{pred}@VT$ and the predicted electrical activity $EAdi_{pred}@VT$.

10. The ventilatory assist level controlling method as defined in claim 9, comprising:
    calculating a neuromechanical efficiency of the respiratory system of the patient $NMERS_{assist}$ for the assisted breath of the patient as a function of a neurally adjusted ventilatory assist (NAVA) level and the neuromechanical efficiency $NMERS_{no\text{-}assist}$.

11. The ventilatory assist level controlling method as defined in claim 10, comprising:
    calculating at least one of the ratios $NMERS_{no\text{-}assist}/NMERS_{assist}$ and $NMERS_{assist}/NMERS_{no\text{-}assist}$.

12. The ventilatory assist level controlling method as defined in claim 9, comprising determining a given pressure value $P_{vent}$ corresponding to the tidal volume of the patient and subtracting the given pressure value $P_{vent}$ from the predicted pressure $P_{pred}@VT$ to obtain an inspiratory pressure $P_{pat\text{-}pred}$ contributed by the patient, and calculating, at the tidal volume of the patient, a contribution of the patient $P_{pat}\% \text{ VT}$ to inspiratory pressure using the following relation: $P_{pat}\% \text{ VT}=(P_{pat\text{-}pred}/P_{vent})\times 100$, and wherein controlling the mechanical ventilator comprises:

inputting a target $P_{pat}\% \text{ VT}_{target}$;

comparing the contribution of the patient $P_{pat}\% \text{ VT}$ to the target $P_{pat}\% \text{ VT}_{target}$; and modifying the NAVA level in response to the comparison.

13. The ventilatory assist level controlling method as defined in claim 12, wherein controlling the mechanical ventilator comprises:

calculating an initial NAVA level using the predicted pressure $P_{pred}@\text{VT}$, the predicted electrical activity $\text{EAdi}_{pred}@\text{VT}$ and the contribution of the patient $P_{pat}\% \text{ VT}$ to inspiratory pressure.

14. A device for controlling a level of ventilatory assist applied to a patient by a mechanical ventilator, comprising at least one first detector adapted to determine, for each of a plurality of assisted breaths of the patient:

a total measured inspiratory volume, wherein the total measured inspiratory volume is produced by both the patient and the mechanical ventilator, and a difference measured inspiratory volume, wherein the difference measured inspiratory volume is contributed by the mechanical ventilator;

a sensor adapted to provide a measured inspiratory assist pressure produced by the mechanical ventilator;

at least one processor; and a memory coupled to the processor and comprising non-transitory instructions that when executed cause the processor to implement:

a first calculator of a first relation between inspiratory assist pressure values $P_{vent}$ and total inspiratory volume values $V_{assist}$ by building a first curve in which each point corresponds to one of the measured inspiratory assist pressures and to a corresponding one of the total measured inspiratory volumes;

a second calculator of a second relation between the inspiratory assist pressure values $P_{vent}$ and difference inspiratory volume values $V_{vent}$ by building a second curve in which each point corresponds to one of the measured inspiratory assist pressures and to a corresponding one of the difference inspiratory volumes;

a third calculator, using a plurality of points of the first curve and a corresponding plurality of points of the second curve, calculating a plurality of ratios between (i) inspiratory assist pressure values $P_{vent}$ of the second curve at respective difference inspiratory volume values $V_{vent}$ of the second curve and (ii) inspiratory assist pressure values $P_{vent}$ of the first curve at respective total inspiratory volume values $V_{assist}$ of the first curve, wherein the plurality of points of the first curve and the plurality of points of the second curve are selected so that each ratio is calculated using equal values for the total inspiratory volume value $V_{assist}$ and for the difference inspiratory volume value $V_{vent}$; and a multiplier adapted to multiply, for each point of the first curve, the measured inspiratory assist pressure by the ratio corresponding to the total measured inspiratory volume to calculate a third relation between predicted inspiratory pressure values $P_{pred}$ and the total inspiratory volume values $V_{assist}$; and a controller of the mechanical ventilator using the third relation to control the level of ventilatory assist.

15. The ventilatory assist level controlling device as defined in claim 14, comprising:

a second detector of electrical activity $\text{EAdi}_{no\text{-}assist}$ of a respiratory muscle during a non-assisted breath of the patient, and electrical activity $\text{EAdi}_{assist}$ of the respiratory muscle during the assisted breath of the patient.

16. The ventilatory assist level controlling device as defined in claim 15, wherein the respiratory muscle is the diaphragm of the patient.

17. The ventilatory assist level controlling device as defined in claim 14, comprising:

a fourth calculator of the predicted inspiratory pressure $P_{pred}$ at a tidal volume of the patient using the third relation.

18. The ventilatory assist level controlling device as defined in claim 14, comprising:

a subtractor of the measured inspiratory assist pressure at a given total inspiratory volume value $V_{assist}$ from the predicted inspiratory pressure value $P_{pred}$ at the given total inspiratory volume value $V_{assist}$ to obtain an inspiratory pressure value $P_{pat\text{-}pred}$ contributed by the patient.

19. The ventilatory assist level controlling device as defined in claim 18, comprising:

a fifth calculator, at a tidal volume of the patient, of a contribution of the patient $P_{pat}\% \text{ VT}$ to inspiratory pressure using the following relation:

$$P_{pat}\%VT=(P_{pat\text{-}pred}/P_{vent})\times 100.$$

20. The ventilatory assist level controlling device as defined in claim 15, comprising:

a fourth calculator of a predicted electrical activity $\text{EAdi}_{pred}@\text{VT}$ of the respiratory muscle required by the patient to generate a tidal volume using an extrapolating, curve-fitting technique applied to a curve of the electrical activity $\text{EAdi}_{no\text{-}assist}$ versus the inspiratory volume $V_{no\text{-}assist}$.

21. The ventilatory assist level controlling device as defined in claim 20, comprising:

a fifth calculator of a percentage $\text{EAdi} \% \text{ VT}$ of the electrical activity $\text{EAdi}_{no\text{-}assist}$ developed by a respiratory muscle of the patient in relation to the predicted electrical activity $\text{EAdi}_{pred}@\text{VT}$ required for the respiratory muscle of the patient to produce the tidal volume, using the relation:

$$\text{EAdi }\%VT=(\text{EAdi}_{no\text{-}assist}/\text{EAdi}_{pred}@VT)\times 100.$$

22. The ventilatory assist level controlling device as defined in claim 20, comprising:

a sixth calculator of a predicted pressure $P_{pred}@\text{VT}$ at a tidal volume of the patient VT using the third relation; and a seventh calculator of a neuromechanical efficiency of a respiratory system of the patient $\text{NMERS}_{no\text{-}assist}$ for the non-assisted breath of the patient as a function of the predicted pressure $P_{pred}@\text{VT}$ and the predicted electrical activity $\text{EAdi}_{pred}@\text{VT}$.

23. The ventilatory assist level controlling device as defined in claim 22, comprising:

an eighth calculator of a neuromechanical efficiency of the respiratory system of the patient $\text{NMERS}_{assist}$ for the assisted breath of the patient as a function of a neurally adjusted ventilatory assist (NAVA) level and the neuromechanical efficiency $\text{NMERS}_{no\text{-}assist}$.

24. The ventilatory assist level controlling device as defined in claim 23, comprising:

calculating at least one of the ratios $NMERS_{no\text{-}assist}/NMERS_{assist}$ and $NMERS_{assist}/NMERS_{no\text{-}assist}$.

25. The ventilatory assist level controlling device as defined in claim 22, comprising a subtractor of a given pressure value $P_{vent}$ corresponding to the tidal volume of the patient from the predicted pressure $P_{pred}@VT$ to obtain an inspiratory pressure $P_{pat\text{-}pred}$ contributed by the patient, and a calculator, at the tidal volume of the patient, of a contribution of the patient $P_{pat}\%\, VT$ to inspiratory pressure using the following relation: $P_{pat}\%\, VT=(P_{pat\text{-}pred}/P_{vent})\times 100$, and wherein the controller:

receives a target $P_{pat}\%\, VT_{target}$;

compares the contribution of the patient $P_{pat}\%\, VT$ to the target $P_{pat}\%\, VT_{target}$; and modifies the NAVA level in response to the comparison.

26. The ventilatory assist level controlling device as defined in claim 25, wherein the controller calculates an initial NAVA level using the predicted pressure $P_{pred}@VT$, the predicted electrical activity $EAdi_{pred}@VT$ and the contribution of the patient $P_{pat}\%\, VT$ to inspiratory pressure.

* * * * *